(12) United States Patent
Mansi

(10) Patent No.: US 11,759,593 B2
(45) Date of Patent: *Sep. 19, 2023

(54) VENTILATOR SYSTEM WITH SWITCHABLE MECHANICAL AND MANUAL VENTILATORS

(71) Applicant: Imam Abdulrahman Bin Faisal University, Dammam (SA)

(72) Inventor: Ahmed Abdelkarim Mansi, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 27 days.

This patent is subject to a terminal disclaimer.

(21) Appl. No.: 17/698,443

(22) Filed: Mar. 18, 2022

(65) Prior Publication Data

US 2022/0203059 A1 Jun. 30, 2022

Related U.S. Application Data

(63) Continuation of application No. 15/805,568, filed on Nov. 7, 2017, now Pat. No. 11,298,496.

(51) Int. Cl.
| | | |
|---|---|---|
| *A61M 16/08* | (2006.01) | |
| *A61M 39/10* | (2006.01) | |
| *A61M 16/04* | (2006.01) | |
| *A61M 39/22* | (2006.01) | |
| *A61M 16/20* | (2006.01) | |
| *A61M 16/00* | (2006.01) | |

(52) U.S. Cl.
CPC ........ *A61M 16/0816* (2013.01); *A61M 16/04* (2013.01); *A61M 16/0463* (2013.01);
(Continued)

(58) Field of Classification Search
CPC .............. A61M 16/0084; A61M 16/04; A61M 16/0463; A61M 16/0816; A61M 16/201;
(Continued)

(56) References Cited

U.S. PATENT DOCUMENTS

| | | |
|---|---|---|
| 4,240,417 A | 12/1980 | Holever |
| 4,416,273 A | 11/1983 | Grimes |

(Continued)

FOREIGN PATENT DOCUMENTS

CN 103055392 4/2013

OTHER PUBLICATIONS

Endoscopy Support Svcs (ESS), "Endotracheal Tube Adapter for 4~7mm diam. scopes," Apr. 3, 2017, 1 Page.

*Primary Examiner* — Timothy A Stanis
(74) *Attorney, Agent, or Firm* — Oblon, McClelland, Maier & Neustadt, L.L.P.

(57) ABSTRACT

A ventilator adaptor for switching between ventilator devices while maintaining respiratory support to a patient is described. The ventilator adaptor has a first movable element with a first inlet and a second inlet, and a second movable element movably attached to the first movable element and with an outlet. The outlet has an inner diameter of 14.5-15.5 mm, preferably 15 mm, and the first inlet and the second inlet have an outer diameter of 14.5-15.5 mm, preferably 15 mm. The outlet is in fluid communication with the first inlet in a first position or with the second inlet in a second position by moving the second movable element relative to the first movable element thereby aligning the outlet with the first inlet or the second inlet. The outlet may be attached to an endotracheal tube in order to form a ventilation assembly.

6 Claims, 8 Drawing Sheets

(52) U.S. Cl.
CPC ...... *A61M 39/105* (2013.01); *A61M 39/1055* (2013.01); *A61M 39/223* (2013.01); *A61M 16/0084* (2014.02); *A61M 16/20* (2013.01); *A61M 16/201* (2014.02); *A61M 2205/583* (2013.01)

(58) Field of Classification Search
CPC ................ A61M 16/20; A61M 39/105; A61M 39/1055; A61M 39/223; A61M 2205/583
See application file for complete search history.

(56) References Cited

U.S. PATENT DOCUMENTS

| | | |
|---|---|---|
| 4,580,556 A | 4/1986 | Kondur |
| 4,661,110 A | 4/1987 | Fortier |
| 5,692,494 A * | 12/1997 | Pernetti ................ A61M 16/00 128/205.13 |
| 5,735,271 A | 4/1998 | Lorenzen et al. |
| 6,427,374 B1 | 8/2002 | Vaiani |
| 6,615,835 B1 | 9/2003 | Cise et al. |
| 7,191,782 B2 | 3/2007 | Madsen |
| 9,238,115 B2 | 1/2016 | Homuth |
| 2009/0287151 A1 | 11/2009 | Resca |
| 2010/0147310 A1* | 6/2010 | Brewer ............. A61M 16/0463 128/207.14 |
| 2010/0288282 A1 | 11/2010 | Brewer |
| 2011/0139151 A1 | 6/2011 | Burns |
| 2013/0160770 A1 | 6/2013 | Brewer |
| 2015/0151063 A1 | 6/2015 | Hoftman et al. |
| 2015/0352303 A1 | 12/2015 | Godwin |
| 2018/0021533 A1 | 1/2018 | Gausche-Hill |

* cited by examiner

VENTILATOR SYSTEM WITH SWITCHABLE MECHANICAL AND MANUAL VENTILATORS

CROSS-REFERENCE TO RELATED APPLICATIONS

The present application is a Continuation of U.S. application Ser. No. 15/805,568, now allowed, having a filing date of Nov. 7, 2017.

BACKGROUND OF THE INVENTION

Technical Field

The present invention relates to an adaptor for switching between ventilation devices.

Description of the Related Art

Mechanical ventilation is a lifesaving intervention when indicated. Patients with diseases or conditions that lead to acute respiratory failure (ARF) should be connected to a mechanical ventilator by means of a ventilator circuit, until the underlying cause of the ARF is treated or eliminated.

In many cases where mechanical ventilation is required, one or more of the lung areas are collapsed (called lung derecruitment). To treat this, a lung recruitment maneuver is required where a relatively high pressure (30 to 60 cm $H_2O$, or 2.94 to 5.88 kPa) is applied to the lungs for a certain period of time through a closed Patient-Circuit-Ventilator system.

One of the most important components of a ventilation management plan is to maintain a patient's lung recruitment, meaning that all lung segments are kept open and well aerated. Once the lung is recruited from a collapsed state, it is important to minimize significant ventilation interruption and/or circuit disconnection that may lead to recollapse. Continual recruitment and derecruitment of the lungs may lead to conditions such as barotrauma, pneumothorax, and ventilation perfusion mismatch. Furthermore, disconnecting a ventilator circuit may increase the risk of a patient contracting ventilator associated pneumonia (VAP), which has a high mortality rate of 20%-50%.

However, the ventilator circuit may need to be paused or disconnected for different reasons, such as making changes to the ventilator circuit, transferring patients to other departments in or outside a hospital, suctioning or cleaning a patient's airway, providing manual resuscitation, or replacing the mechanical ventilator.

In view of the foregoing, one objective of the present invention is to provide a ventilator adaptor having movable elements with two inlets and an outlet, to enable changes to a ventilator circuit while maintaining a patient's lung recruitment in a closed ventilation system.

BRIEF SUMMARY OF THE INVENTION

According to a first aspect, the present disclosure relates to a ventilator adaptor, comprising a first movable element having a first inlet and a second inlet, and a second movable element movably attached to the first movable element and having an outlet extending in a generally opposite direction from the first movable element. The outlet has an inner diameter of 14.5-15.5 mm, or about 15 mm, and the first inlet and the second inlet have an outer diameter of 14.5-15.5 mm, or about 15 mm. The outlet is in fluid communication with the first inlet in a first position or is in fluid communication with the second inlet in a second position by moving the second movable element relative to the first movable element thereby aligning the outlet with the first inlet or the second inlet.

In one embodiment, the ventilator adaptor has a movable compression seal sandwiched between the first movable element and the second movable element.

In one embodiment, a surface of the first movable element opposite the second movable element is substantially planar, parabolic, or concave, and a first central axis of the first inlet, a second central axis of the second inlet, or both forms an angle of 50°-80° with the surface.

In one embodiment, the first movable element is slidable relative to the second movable element to align the outlet with the first inlet in the first position or the second inlet in the second position.

In one embodiment, the first movable element is rotatable relative to the second movable element to align the outlet with the first inlet in the first position or the second inlet in the second position.

In a further embodiment, the first movable element and the second movable element are disc-shaped.

In one embodiment, the ventilator adaptor, which, other than the first inlet, the second inlet, and the outlet, does not have an additional inlet or outlet.

In one embodiment, the ventilator adaptor has a third inlet on the first movable element.

In one embodiment, an intermediary position of the outlet between the first position and the second position establishes fluid communication simultaneously among the first inlet, the second inlet, and the outlet.

In one embodiment, no intermediary position of the outlet between the first position and the second position establishes fluid communication simultaneously among the first inlet, the second inlet, and the outlet.

In one embodiment, the ventilator adaptor has a cap configured to cover the first inlet, the second inlet, or both independently.

In a further embodiment, the cap comprises a tether attached to a crossbar connected to both the first inlet and the second inlet, wherein the cap is configured to independently cover the first inlet or the second inlet.

In one embodiment, at least one selected from the group consisting of the first inlet, the second inlet, and the outlet comprises a rotatable joint.

In one embodiment, a surface of the first movable element opposite the second movable element is substantially planar, and a section of the first inlet or the second inlet is angled or curved, so that a distal edge of the first inlet or the second inlet circumscribes a plane forming an angle of 60°-90° with the surface.

In one embodiment, the ventilator adaptor has a switch to lock the first movable element relative to the second movable element.

In one embodiment, the ventilator adaptor has a label, a notch, or a groove to indicate an alignment of the first movable element with respect to the second movable element in the first position or in the second position.

According to a second aspect, the present disclosure relates to a ventilation assembly comprising the ventilator adaptor of the first aspect and an endotracheal tube removably attached to the outlet.

According to a third aspect, the present disclosure relates to a method for switching between ventilator devices with the ventilation assembly of the second aspect, while respiratory support through the endotracheal tube is maintained. This method involves:

providing respiratory support by fluidly connecting the endotracheal tube with a first ventilator device fluidly connected to the first inlet, wherein the outlet is in the first position;

connecting a second ventilator device to the second inlet;

moving the outlet from the first position to the second position thereby providing respiratory support by fluidly connecting the endotracheal tube with the second ventilator device; and disconnecting the first ventilator device from the first inlet.

In one embodiment of the method, the first ventilator device is a mechanical ventilator, and the second ventilator device is a manual resuscitator device.

In one embodiment of the method, the endotracheal tube is disposed within a patient, and a lung recruitment of the patient is maintained from before the moving to after the moving.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
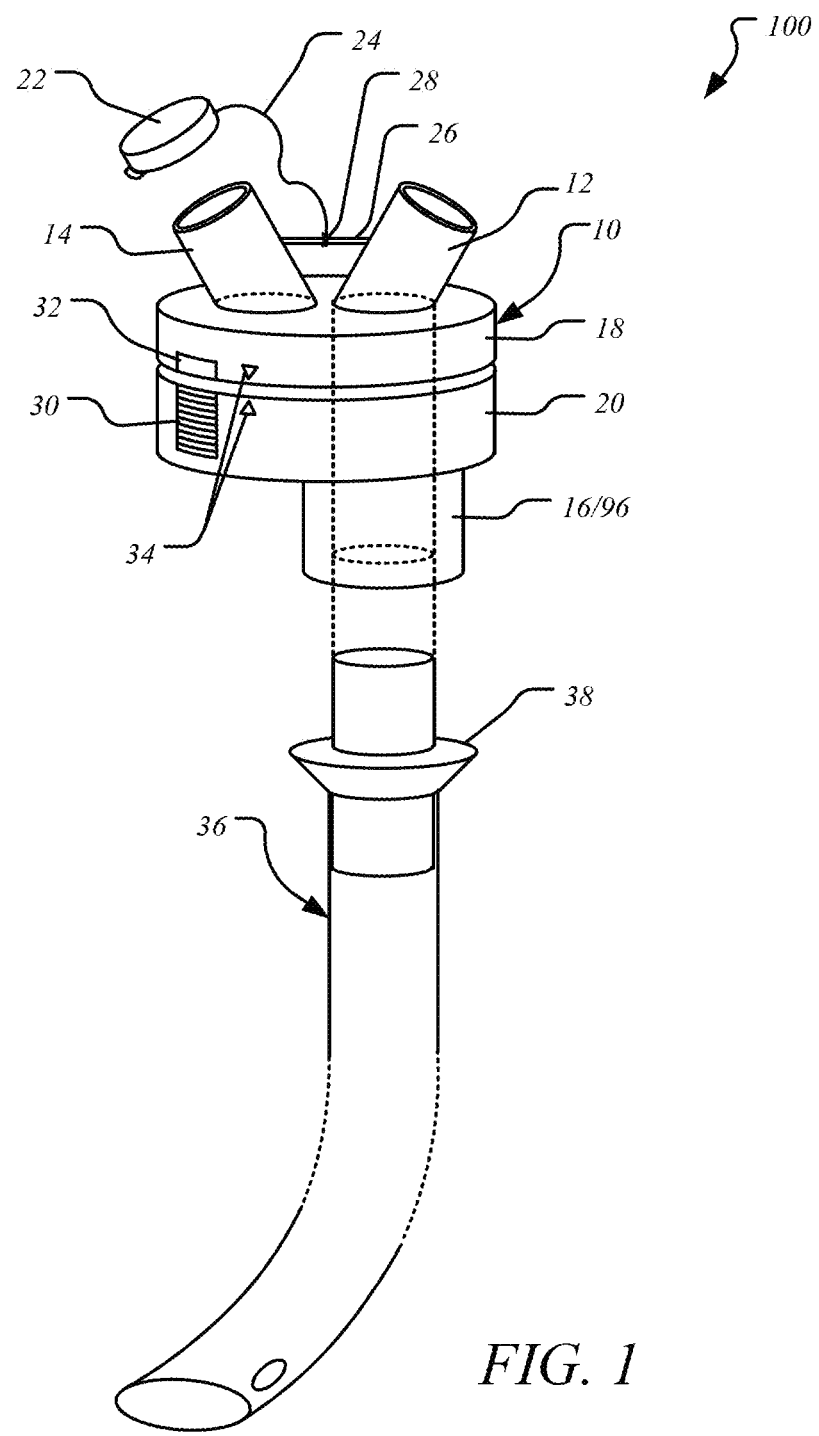
FIG. 1 is the ventilator adaptor with an endotracheal tube.

Embodiments of the present disclosure will now be described more fully hereinafter with reference to the accompanying drawings, in which some, but not all embodiments of the disclosure are shown. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out. For convenience of description, directional terms such as "down," "horizontally," "vertically," etc. refer to the orientation of the ventilator adaptor as depicted in FIG. 1. Also, the term "inlets" refers to both the first inlet and the second inlet.

Figure 2:
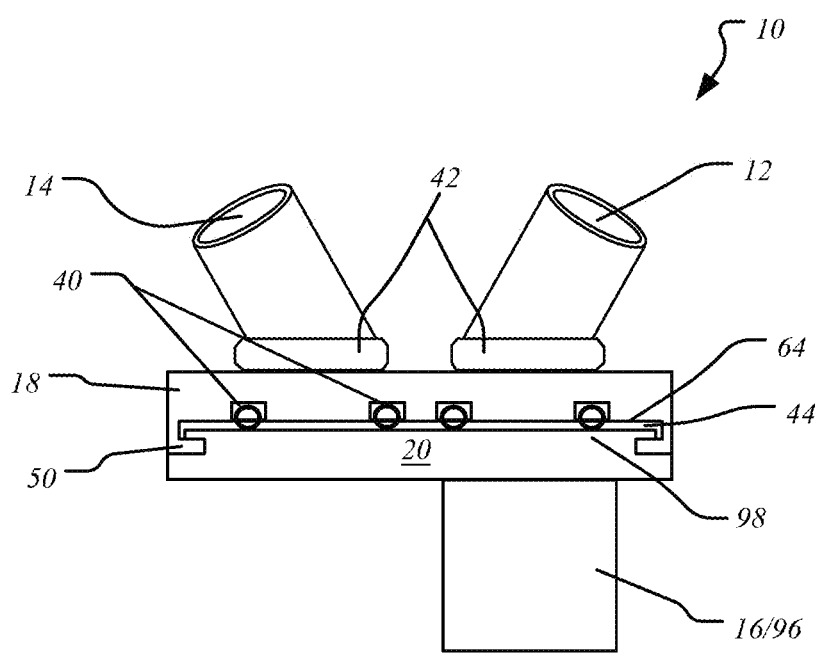
FIG. 2 is a ventilator adaptor having rotatable elements.
Figure 3A:
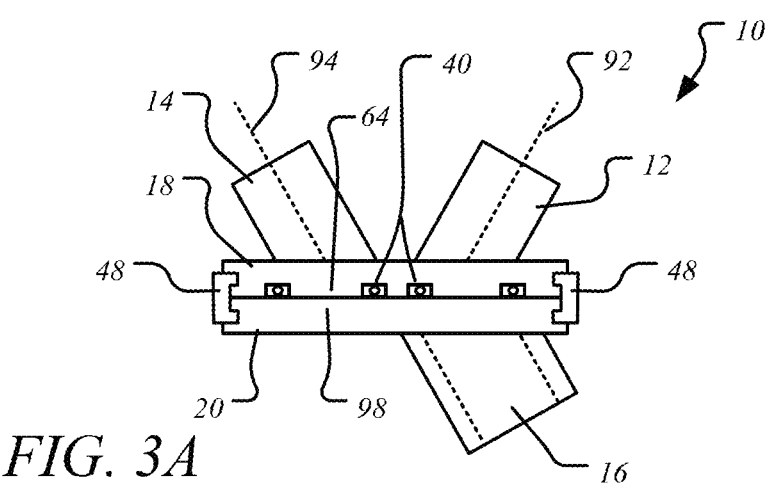
FIG. 3A is a cross-section view of a ventilator adaptor having inlets and an outlet at angles, and an annular collar.
Figure 5A:
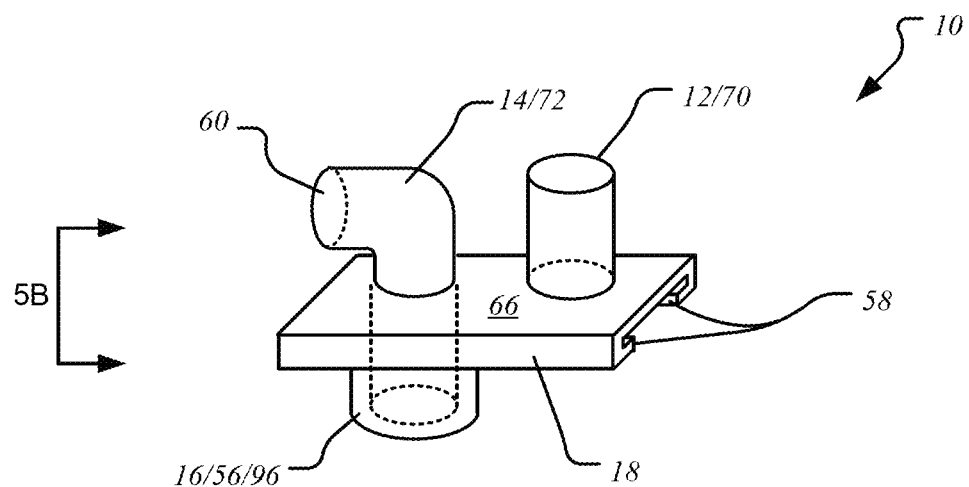
FIG. 5A is a slidable ventilator adaptor in a second position.
Figure 5B:
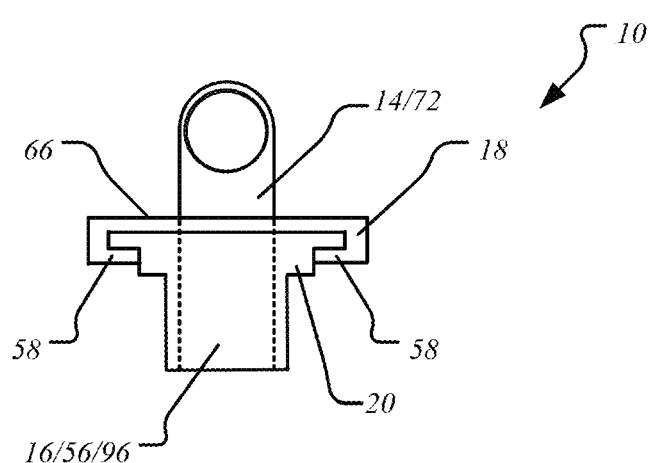
FIG. 5B is a side view of the slidable ventilator adaptor of FIG. 5A.

According to a first aspect, the present disclosure relates to a ventilator adaptor 10, comprising a first movable element 18 having a first inlet 12 and a second inlet 14, and a second movable element 20 movably attached to the first movable element 18 and having an outlet 16 extending in a generally opposite direction from the first movable element 18. An example ventilator adaptor 10 is shown in FIG. 1. Preferably, a bottom surface of the first movable element 64 (i.e., inlet junction) and the top of the second movable element 98 (i.e., outlet junction) are proximal to each other and substantially planar, where the term "substantially planar" refers to height variations along any given section (e.g., sections of about 10 mm in diameter or less) of the surface, excluding the structure of the inlets and outlet, being reduced to about 3 mm or less. The inlet junction 64 may also be thought of as the contact surface of the first movable element 18, with the outlet junction 98 being the surface of the second movable element directly facing it. In one embodiment, the inlet junction 64 and the outlet junction 98 are substantially planar and substantially parallel, wherein two lines, one normal to the inlet junction, and the other normal to the outlet junction, would together form an angle of 0°-3°, preferably 0°-2°, more preferably 0°-1°, where an angle of 0° denotes exactly parallel inlet and outlet junctions. In another embodiment, the inlet junction 64 and the outlet junction 98 are parabolic or concave. The inlet junction 64 and the outlet junction 98 may be in contact with each other, or spaced by a gap 44 of 0.2-2 mm, preferably 0.4-1.5 mm, more preferably 0.5-1.1 mm. FIG. 2 shows a cross-section view of a ventilator adaptor 10 with such a gap 44, while FIGS. 3A and 5B show cross-section views of a ventilator adaptor 10 where the inlet junction 64 and outlet junction 98 are in direct contact with each other without a gap. As defined here, the outlet 16 extending in a generally opposite direction from the first moveable element 18 means that the outlet 16 extends away from the inlet junction 64.

In one embodiment, the ventilator adaptor 10 may comprise polypropylene, polyethylene, polymethylmethacrylate, polyether ether ketone, polycarbonate, stainless steel, titanium, titanium alloy, carbon fiber, polytetrafluoroethylene (PTFE), ultra-high-molecular-weight polyethylene (UHMWPE), polylactic acid (PLA), poly(lactic-co-glycolic acid) (PLGA), polyethylene terephthalate (PET), acrylonitrile butadiene styrene (ABS), polytetrafluoroethylene (PTFE), glass, ceramic, or some other biocompatible material. In one embodiment, the ventilator adaptor 10 may be intended for single use. In a further embodiment, a ventilator adaptor 10 intended for single use may be sterilized, for example, by gamma ray radiation or ethylene oxide exposure, and may be packaged separately in sterile packaging. In another embodiment, the ventilator adaptor 10 may comprise stainless steel or a heat-resistant plastic, and may be autoclaved between multiple uses. The ventilator adaptor 10 may have sidewall thicknesses of 0.5-4.0 mm, preferably 0.6-3.0 mm, more preferably 0.7-1.5 mm.

In one embodiment, a movable compression seal is sandwiched between the first movable element 18 and the second movable element 20. For instance, this seal may be an O-ring 40 fit into a groove in the inlet junction 64 or the outlet junction 98. The seal may comprise an elastomeric material, such as silicone rubber, latex, butyl rubber, neoprene, and/or nitrile. Preferably the seal is made of a material that can be compressed and moved across a surface, without degrading or losing its pressure resistance. The seal may be located along a perimeter of either of the inlets or the outlet. In a further embodiment, a second seal may be located along a perimeter of either the inlet junction or the outlet junction and encircle or contain both inlets. FIGS. 2 and 3A show cross-section views of a ventilator adaptor 10 with O-rings 40.

In one embodiment, the outlet 16 has an inner diameter of 14.0-16.0 mm, 14.5-15.5 mm, or preferably about 15 mm, and an outer diameter of 16-26 mm, preferably 18-24 mm, more preferably 20-23 mm. The first inlet 12 and the second inlet 14 ("inlets") each have an outer diameter of 14.0-16.0 mm, preferably 14.5-15.5 mm, or about 15 mm, and an inner diameter of 5.0-15.5 mm, preferably 10.0-14.7 mm, more preferably 12.0-14.5 mm. In a preferred embodiment, the inlets 12/14 and the outlet 16 are shaped to accept standard respirator fittings, with the inlets having outer diameters of about 15 mm, and the outlet having an inner diameter of about 15 mm. The ventilator adaptor 10 may have a similar appearance and size as a heat moisture exchanger (HME). In one embodiment, the inlets 12/14 are 15 mm M connectors (also known as 15M connectors), and the outlet 16 is a 22 mm M/15 mm F connector (also known as a 22M/15F connector). These connectors may allow respiratory or ventilator devices to connect to the ventilator adaptor 10 by frictional coupling. These devices may connect directly to the ventilator adaptor 10 or through a length of tubing, for example, 0.3-2.0 m long, or 1.0-1.5 m long. Examples of respiratory or ventilator devices include, but are not limited to, a manual resuscitator device 86 (also known as a resuscitator bag), an automatic resuscitator, a gas tank, and a mechanical ventilator 84 (including transport ventilators, intensive-care ventilators, and neonatal ventilators).

In one embodiment, either of the inlets 12/14 or the outlet 16 may be removably attached to the first movable element 18 or the second movable element 20, for instance, through frictional coupling, screw threads, or a bayonet mount.

In an alternative embodiment, other standardized respirator connectors may be used such as 22M, 22F, a Luer lock, a 30 mm outlet, a 7.6 mm port, or an 8 mm spigot. In another alternative embodiment, attachments to either of the inlets 12/14 or the outlet 16 on the ventilator adaptor 10 may be possible with screw thread connectors, clips, clamps, magnets, ties, bands, or clasps.

Figure 6:
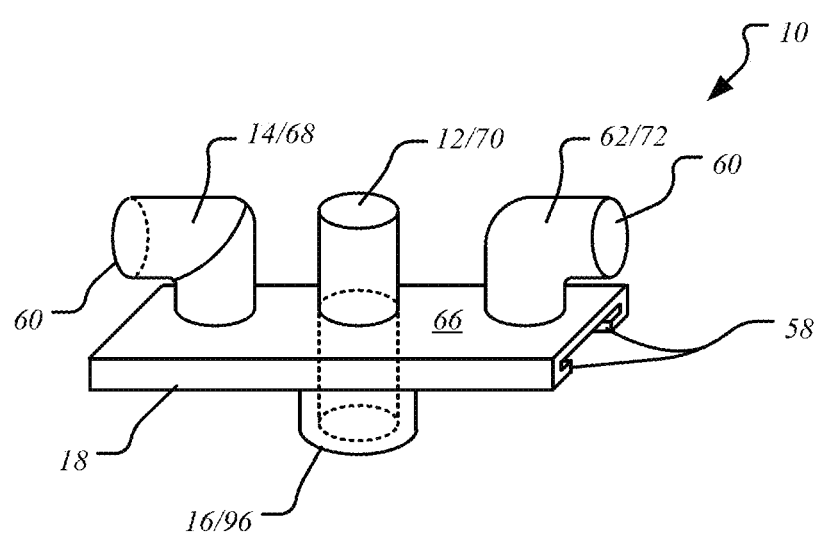
FIG. 6 is a slidable ventilator adaptor having a third inlet.

In one embodiment, the ventilator adaptor 10 has a third inlet 62 on the first movable element 18 or a second outlet 46 on the second movable element 20. For example, FIG. 6 shows a ventilator adaptor 10 with a third inlet 62 on the first movable element 18, and FIG. 2 shows a ventilator adaptor 10 with a second outlet 46 on the second movable element 20. In another embodiment, the ventilator adaptor 10, which, other than the first inlet 12, the second inlet 14, and the outlet 16, does not have an additional inlet or outlet, such as the ventilator adaptor 10 shown in FIGS. 1, 3A, 3B, and 5A.

The inlets 12/14 and the outlet 16 may be cylindrically shaped with lengths of 10-55 mm, preferably 12-25 mm, more preferably 15-20 mm. In one embodiment, the first inlet 12, the second inlet 14, and/or the outlet 16 may be in the form of right cylinders, having a central axis and sides substantially perpendicular to the inlet junction 64 or to the outlet junction 98, and with the same cross-section area throughout the length of the cylinder. In some embodiments, the inlets 12/14 and/or the outlet 16 may have a length shorter than 25 mm as a connector may not need to fit over or into an entire 25 mm or greater length. As defined here, "substantially perpendicular" refers to two elements forming an angle of 86°-90°, preferably 87°-90°, more preferably 89°-90°, where 90° is perpendicular. These embodiments are shown in FIGS. 1, 2, 5A, 5B, and 6, which have at least one substantially perpendicular inlet 70 or outlet 96.

Figure 3B:
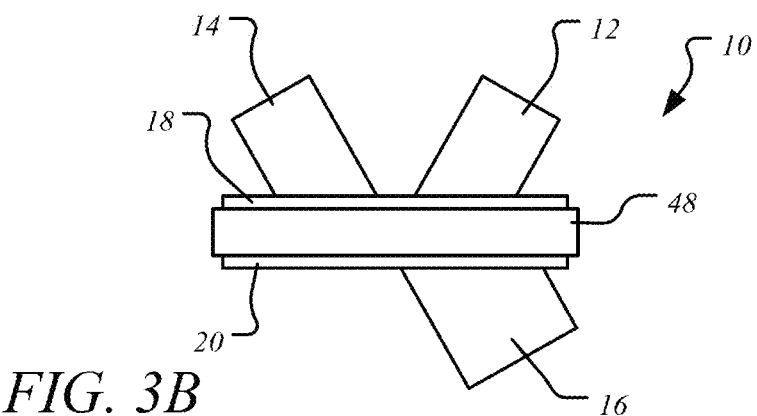
FIG. 3B is the exterior view of the ventilator adaptor of FIG. 3A.

In another embodiment, the first inlet 12, the second inlet 14, and/or the outlet 16 may be in the form of a truncated cylinder, where the truncation occurs at the attachment of the first inlet 12 and/or the second inlet 14 to the first movable element 18, or at the attachment of the outlet 16 to the second movable element 20, so that each distal edge of the first inlet, the second inlet, and the outlet still encircles a plane perpendicular to each central axis. In other words, in this embodiment, the first inlet 12, the second inlet 14, and/or the outlet 16 has the form of a truncated cylinder with a central axis that is not substantially perpendicular to the inlet junction 64 or the outlet junction 98. These embodiments are shown in FIGS. 1, 3A, and 3B. In one embodiment, a first central axis 92 of the first inlet 12, or a second central axis 94 of the second inlet 14, or both forms an angle of 50°-80°, preferably 55°-75°, more preferably 60°-70° with the surface of the inlet junction 64. In a preferred embodiment, the first central axis 92 and the second central axis 94 form angles of 60°-70° with the inlet junction 64. These angles may help avoid interference between simultaneous connections on both inlets 12/14, while allowing small diameters or small horizontal dimensions of the first movable element 18 and the second movable element 20.

In an alternative embodiment, the outlet 16 may be formed completely inside the second movable element 20, for example as a hole with a depth of 10-55 mm, preferably 12-25 mm, more preferably 15-20 mm, and a diameter of 14.5-15.5 mm, preferably about 15 mm, or as a hole otherwise sized to accept a 15M fitting partially or completely inserted. This embodiment would require that the second movable element has a thickness at least as large as the hole's depth.

In one embodiment, a surface of the first movable element opposite the second movable element is substantially planar (i.e. this surface being the inlet junction 64), and a section of the first inlet or the second inlet is angled or curved, so that a distal edge 60 of the first inlet or the second inlet circumscribes a plane forming an angle of 60°-90°, preferably 65°-90°, more preferably 75°-90° with the surface 64. In one embodiment, the distal edge 60 circumscribes a circle that is substantially perpendicular to the inlet junction 64. In these embodiments, one or more inlets 12/14 does not extend along a linear central axis, but along a curved or angled path. FIGS. 5A and 6 show an angled inlet 68 and/or a curved inlet 72. In other embodiments, a single inlet may be both curved and angled, or shaped in other means in order that the distal edges circumscribe planes having angles as previously mentioned.

In one embodiment, the inlets 12/14 or the outlet 16 may not comprise the same cross-section area or shape throughout their entire length. For instance, a portion of the inlets or the outlet may have more than one diameter throughout its length, or may have a continually varying diameter, for instance, as a conical segment. In one embodiment, one or more inlets 12/14 or the outlet 16 may connect to the first movable element 18 or the second movable element 20 through a segment having a diameter 20%-80% smaller, preferably 30%-70% smaller, more preferably 40%-60% smaller than a portion adjacent to a distal edge. In one embodiment, this smaller segment may have a length of 10-40 mm, preferably 15-35 mm, more preferably 18-30 mm. In a further embodiment, this smaller segment may comprise a flexible tubing material so that either of the inlets 12/14 or the outlet 16 may be movable in different angles while attached to the first movable element 18 or the second movable element 20.

In one embodiment, one or more of the inlets 12/14 or the outlet 16 has a rotatable joint 42. This rotatable joint 42 may be at the attachment of either of the inlets 12/14 or the outlet 16 to the first movable element 18 or the second movable element 20, respectively, or may be somewhere along either of the inlets 12/14 or the outlets 16 at a position between that attachment and a distal end. FIG. 2 shows inlets 12/14 each having a rotatable joint 42 comprising a collar. Here, the collar connects together two segments of each inlet 12/14 to allow rotation while preventing air leaks. In another embodiment, two segments may be joined by nesting an annular flange of one segment into an annular groove of the other segment.

Figure 8:
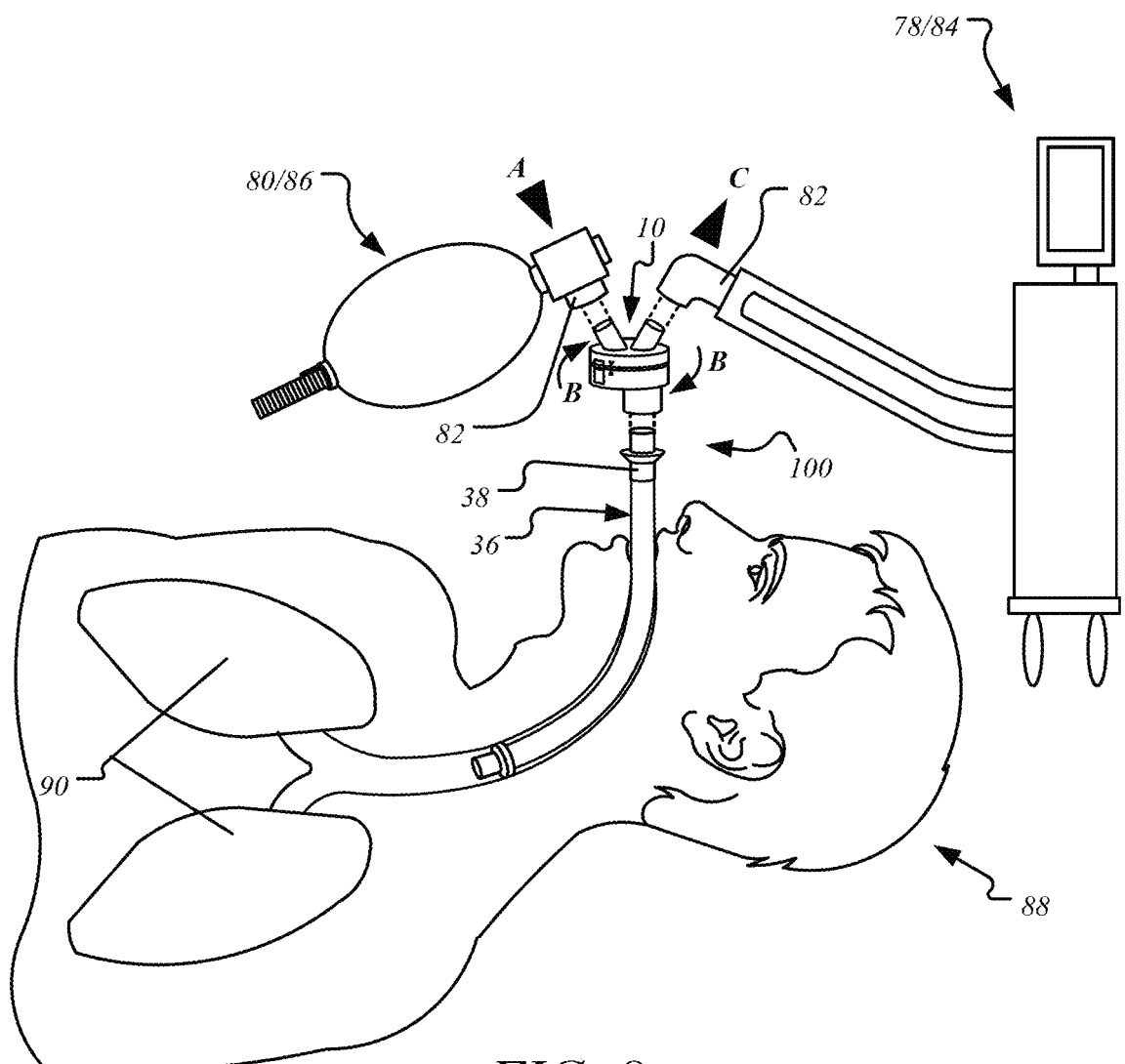
FIG. 8 shows a ventilation assembly (with a manual resuscitator) being used with ventilator devices and having an endotracheal tube inserted into a patient.

According to a second aspect, the present disclosure relates to a ventilation assembly 100 comprising the ventilator adaptor 10 of the first aspect and an endotracheal tube 36 removably attached to the outlet 16 of the ventilator adaptor. In other embodiments, different ventilation assemblies may be possible with one or more of the inlets 12/14 or outlet 16 forming a permanent connection with a ventilator device 78/80, an endotracheal tube 36, or some accessory device. For example, the ventilator adaptor 10 may be formed and packaged as a ventilation assembly 100 with an endotracheal tube 36 adhered to the outlet 16. In other embodiments, the ventilator adaptor 10 may have or be packaged as a ventilation assembly 100 with an endotracheal tube 36 removably attached to the outlet 16. The endotracheal tube 36 may comprise a tubing with a smaller diameter connected to a barbed fitting of an adaptor 38 having a distal 15M fitting configured to fit into the outlet 16 having a 22M/15F connector. FIGS. 1 and 8 show ventilation assemblies 100 comprising ventilator adaptor 10 and endotracheal tubes 36. Alternative ventilation assemblies may be possible with one or more accessory devices, such as those previously mentioned. One or more accessory devices may be removably or permanently attached to a ventilator adaptor 10 at one or more of the inlets 12/14 or outlet 16, or at some other location on the ventilator adaptor 10.

An endotracheal tube 36 is a type of catheter inserted into the trachea through the mouth (orotracheal) or nose (nasotracheal) of a patient for the primary purpose of establishing and maintaining a clear airway and to also ensure an adequate exchange of oxygen and carbon dioxide. Endotracheal tubes 36 may be used to deliver oxygen in higher concentrations than found in air, or to administer other gases such as helium, nitric oxide, nitrous oxide, xenon, or certain volatile anesthetic agents such as desflurane, isoflurane, or sevoflurane. Endotracheal tubes 36 may also be used as a route for administration of certain medications including, but not limited to, salbutamol, atropine, epinephrine, ipratropium, and lidocaine, in vaporous or aerosol (droplet) states. Endotracheal tubes 36 are commonly used for airway management in the settings of general anesthesia, critical care, mechanical ventilation, and emergency medicine.

Endotracheal tubes 36 may be constructed of or comprise polyvinyl chloride, silicone rubber, latex rubber, stainless steel or other biocompatible material. Most endotracheal tubes 36 have an inflatable cuff to seal the trachea and bronchial tree against air leakage and aspiration of gastric contents, blood, secretions, and other fluids. Alternatively, endotracheal tubes 36 may be uncuffed, especially for pediatric patients. Endotracheal tubes 36 may be configured for oral or nasal entry, may be preformed, reinforced with a metal wire or other rigid material, labeled with a contrast agent or radio opaque material, or may be configured as double-lumen endobronchial tubes, which allow single-lung ventilation while one lung is collapsed for a surgical procedure. Endotracheal tubes 36 may also have a beveled tip, an additional hole at the tip (called a "Murphy eye") to prevent blockage, and/or length markings. Endotracheal tubes 36, such as RAE tubes, may have preformed curves in order to be used in south facing or north facing insertion.

For human patients, endotracheal tubes 36 range in size from 2-10.5 mm in inner diameter, with adult patients generally using tubes with inner diameters of 6.5-9.5 mm, preferably 7.0-9.0 mm. Endotracheal tubes 36 for human patients may have wall thicknesses of 0.7-1.8 mm, preferably 0.8-1.7 mm, more preferably 0.9-1.3 mm, and may have lengths or insertion depths of 5-30 cm, preferably 15-27 cm, more preferably 20-24 cm. Endotracheal tubes larger than 6 mm inner diameter usually have an inflatable cuff. Another type of endotracheal tube 36 has an opening above the inflatable cuff, which can be used for suction of the nasopharngeal area, which helps reduce the risk of chest infections in long-term intubated patients.

In alternative embodiments, where maintaining lung recruitment may not be a goal, a respirator or resuscitation mask may be attached to the outlet 16 and may be configured to cover the nose and/or mouth of a patient. In additional alternative embodiments, a nasal cannula, a tracheotomy or tracheostomy tube, a tracheal tube introducer (a "bougie"), or a tracheal button may be attached to the outlet 16. In an alternative embodiment, the outlet may be attached to a chamber, such as a glove box, a hyperbaric chamber or oxygen tent, a hypobaric chamber, a decompression chamber, or a recompression chamber.

As mentioned previously, an accessory device may attach to one or more of the inlets 12/14 or the outlet 16. A ventilator adaptor 10 with an accessory device permanently or removably attached may be considered as an alternative type of a ventilation assembly. Alternatively, an accessory device may attach elsewhere on the ventilator adaptor 10, such as through the first movable element 18 or an access port, and have fluid communication with one or more of the inlets 12/14 or the outlet 16. The accessory device may be an inline manometer, a filter, a one-way valve such as a positive end expiratory pressure (PEEP) valve, a thermometer, a hygrometer, a flow meter, a syringe, or an access port. An access port may be used for a catheter, a suction device, or as a means of administering vaporous or liquid medicines to a patient. An access port may also be used to insert a camera to allow visual examination of the respiratory tract.

In one preferred embodiment, the ventilator adaptor 10 has no air leak. However, in an alternative embodiment, the ventilator adaptor 10 may have a leak rate of less than 25 mL/min, preferably less than 15 mL/min, more preferably less than 10 mL/min. In one embodiment, the ventilator adaptor 10 may be able to withstand interior pressures of 16 kPa or less, preferably 14 kPa or less, more preferably 12 kPa or less. Generally, mechanical ventilators are provided with safety mechanisms to prevent high airway pressure. However in an alternative embodiment, the ventilator adaptor 10 may be designed with an additional valve that opens to relieve a higher pressure, or a valve that is always open to relieve some amount of pressure continually. Such an additional valve may ensure that a continuous positive pressure is applied to a patient 88. In one embodiment, the ventilator adaptor may handle flow rates that create the previously mentioned pressures, or flow rates of up to 60

L/min, preferably up to 40 L/min, more preferably up to 30 L/min. Preferably, the ventilator adaptor is able to handle inspiratory flow rates of about 40-60 L/min, though for some patients, the inspiratory flow rate may be above or below that range. Preferably, the ventilator adaptor is able to handle expiratory flow rates of up to 100 L/min, though for some patients, the expiratory flow rate may be greater than 100 L/min.

In one embodiment, the ventilator adaptor 10 has a cap 22 configured to cover the first inlet 12, the second inlet 14, or both independently. This cap 22 may have similar inner and outer diameters as mentioned previously for the outlet 16, and may have a depth of 5-20 mm, preferably 7-15 mm, more preferably 8-10 mm. Preferably the cap 22 can secure to and cover the distal edge of one or more inlet 12/14 by means of frictional coupling, though in an alternative embodiment, the cap 16 may fit by means of a screw thread or some other structure. Preferably the cap 16 is able to cover an inlet, in order to keep the inlet clean and/or sterile. For instance, the cap 16 may not need to stay secure against pressure differences, as it may be intended to only cover an inlet not actively engaged in ventilation. However, in an alternative embodiment, cap 16 may stay secured against differences in pressure, for instance, being able to withstand pressure differences of up to 5.0 kPa, preferably up to 4.0 kPa, more preferably up to 3.0 kPa. The cap 16 may comprise materials previously mentioned for the ventilator adaptor 10, and/or elastomeric materials such as those listed for the compressible seal 40. Preferably the cap 16 comprises silicone or rubber in order to assist in both fitting and sealing of the cap to the inlet. In one embodiment, the cap 16 comprises a tether 24 to connect with the rest of the ventilator adaptor 10. This tether 24 may be a strip of material such as those previously mentioned for the ventilator adaptor 10 or compressible seal 40, and may have a width of 2-10 mm, preferably 2.5-9 mm, more preferably 3-8 mm, and a length of 5-20 cm, preferably 5-15 cm, more preferably 5-8 cm. The tether 24 may be connected to a ring rotatably attached on a circumference of either of the inlets 12/14, or the tether may be connected to either first 18 or second 20 movable elements, or to a connecting collar 48. In one embodiment, the tether 24 is attached to a crossbar 26, and may furthermore be slidably attached by terminating in a loop 28 that encircles a part of the crossbar 26. The crossbar 26 may be connected to the first inlet 12 and the second inlet 14, or may be connected elsewhere, such as on the first movable element 18. The crossbar 26 may have a length of 0.5-3 cm, preferably 0.7-2.5 cm, more preferably 0.8-2.3 cm and a diameter of 0.2-3 mm, preferably 0.5-2 mm, more preferably 0.6-1.5 mm. In one embodiment, where the tether 24 is attached to a crossbar 26 connected to both inlets 12/14, the cap 22 is able to cover both inlets 12/14 independently. This configuration of the cap 22, tether 24, and crossbar 26 is shown in FIG. 1.

In an alternative embodiment, the cap 16 may be able to fit on both inlets 12/14 and the outlet 16 independently. Where the inlets 12/14 are 15M connectors, and the outlet 16 is a 22F/15M connector, the cap 16 may comprise one or more raised concentric rings that allow it to interface with both types of connectors. Alternatively, one side of the cap may fit 15M connectors, while the opposing side fits 22F/15M connectors. In another alternative embodiment, an elongated cap 22 may be able to cover both inlets 12/14 simultaneously. In another embodiment, a cap 22 may comprise an additional adaptor or an access port.

As mentioned previously, the first movable element 18 and the second movable element 20 are movably attached to each other. The outlet 16 is in fluid communication with the first inlet 12 in a first position 52 or is in fluid communication with the second inlet 14 in a second position 56 by moving the second movable element 20 relative to the first movable element 18 (or vice versa) thereby aligning the outlet 16 with the first inlet 12 or the second inlet 14. Furthermore, the outlet in the first position 52 has no fluid communication with the second inlet 14, and the outlet in the second position 56 has no fluid communication with the first inlet 12. This moving may be performed by sliding or rotating the first movable element 18 relative to the second movable element 20. In an alternative embodiment, the moving may involve both sliding and rotating, for example, where the moving engages or disengages a lock. In another alternative embodiment, the moving may involve other movements such as tilting, pressing, or pulling the first movable element 18 relative to the second movable element 20.

In one embodiment, the first movable element 18 has a third inlet 62, and a third position is possible which aligns the outlet 16 with the third inlet 62, establishing fluid communication between the outlet 16 and the third inlet 62.

Figure 7A:
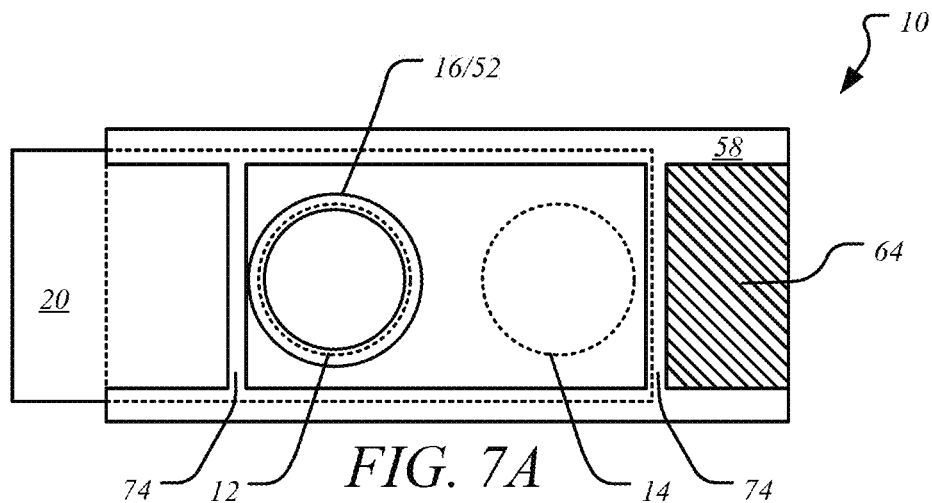
FIG. 7A is a bottom view of a slidable ventilator adaptor in a first position.
Figure 7B:
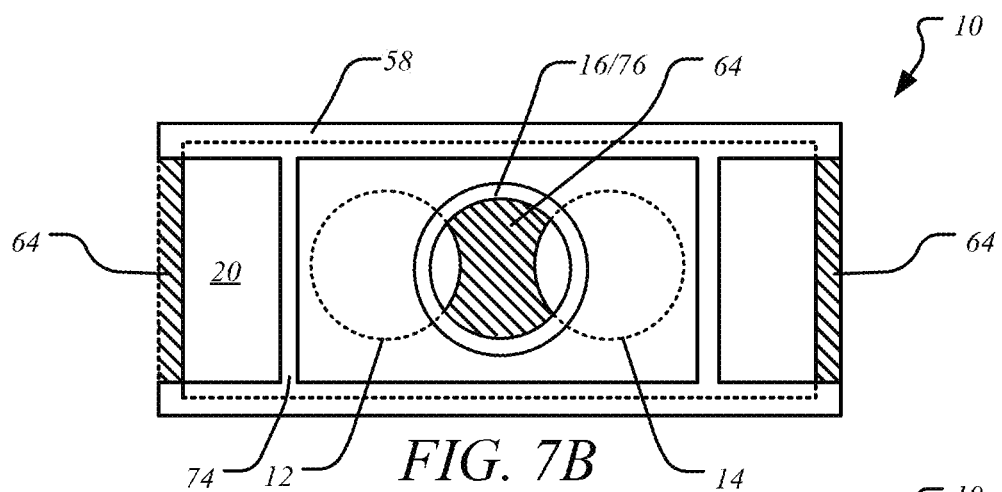
FIG. 7B is a bottom view of the slidable ventilator adaptor in an intermediary position having simultaneous fluid communication among the inlets and the outlet.
Figure 7C:
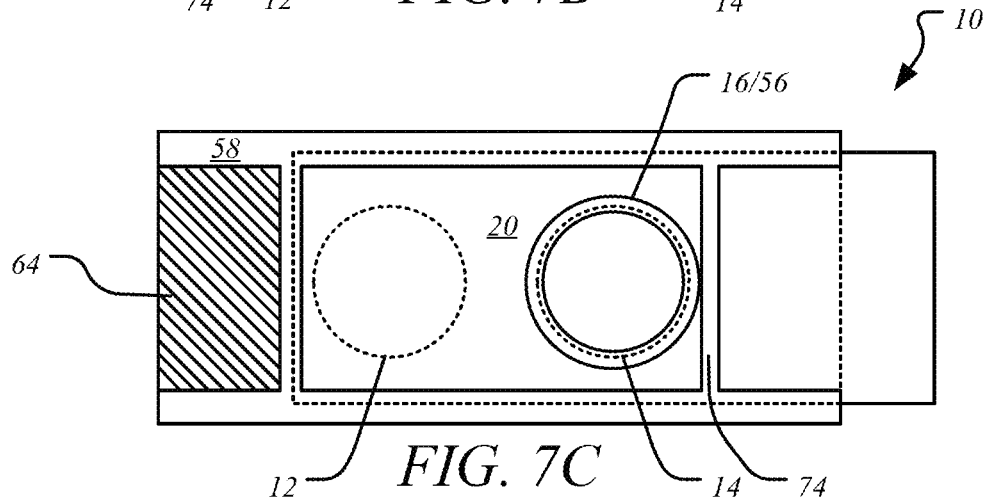
FIG. 7C is a bottom view of the slidable ventilator adaptor in a second position.

In one embodiment, an intermediary position 76 of the outlet 16 between the first position 52 and the second position 56 establishes fluid communication simultaneously among the first inlet 12, the second inlet 14, and the outlet 16. An example of this is shown in FIG. 7B, which is an intermediary position 76 of the outlet 16 between the first position 52 in FIG. 7A and the second position 56 in FIG. 7C. FIG. 7B shows that the outlet 16 opens to portions of both inlets 12/14 at the same time, which thus establishes fluid communication among both inlets 12/14 and the outlet 16. However, depending on the spacing of the inlets 12/14 relative to the range of the outlet's movement, a ventilator adaptor 10 that has an outlet intermediary position that simultaneously establishes fluid communication among the inlets and the outlet may have additional intermediary positions that do not establish such fluid communication. For instance, the first 18 and second 20 movable elements may be moved one way through an intermediary position 76 with the simultaneous fluid communication, but moved another way without encountering such intermediary position. This movement may occur when the first 18 and second 20 movable elements are rotated in different directions, as the outlet 18 may encounter different circumferential spacing between inlets 12/14 if the inlets are not arranged with two-fold rotation symmetry.

In one embodiment, one or more of the inlets 12/14 or the outlet 16 may have a valve to limit or completely shut off the flow of air. In one alternative embodiment, where an intermediary position 76 is possible for simultaneous fluid communication among the inlets 12/14 and the outlet 16, a ventilator adaptor 10 having valves in both inlets 12/14 may not need to have movable elements, as the flow path may be determined by independently operating those valves. This way, a first position 52 and second position 56 of the outlet 16 may be achieved without having to move first 18 and second 20 movable elements relative to each other. In this alternative embodiment, the ventilator adaptor 10 may be formed as a Y-shape.

Figure 4A:
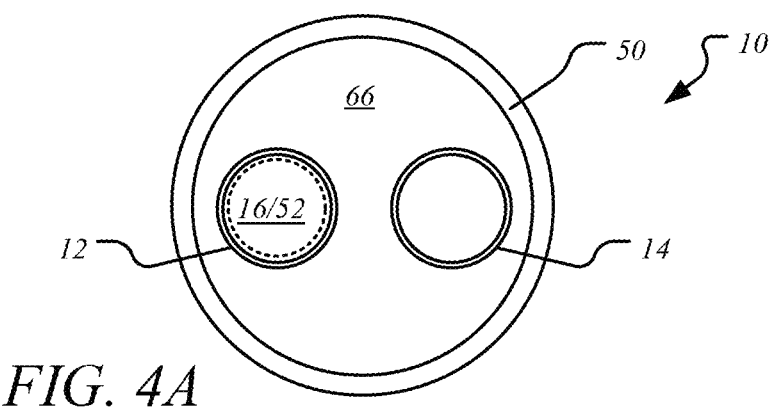
FIG. 4A is a top view of a rotatable ventilator adaptor in a first position.
Figure 4B:
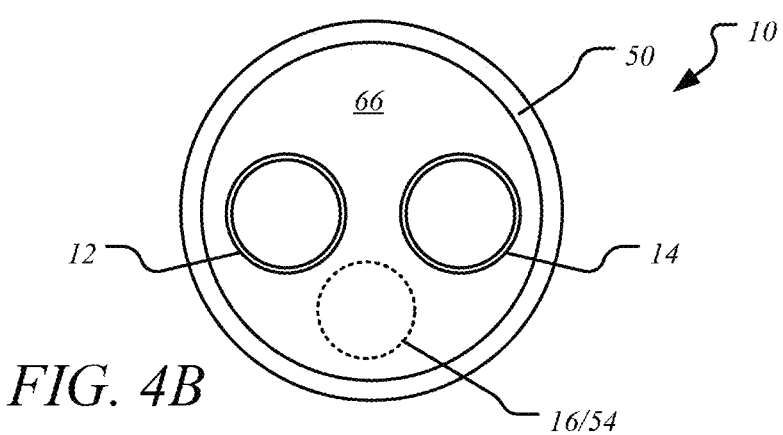
FIG. 4B is a top view of the rotatable ventilator adaptor in an intermediary position.
Figure 4C:
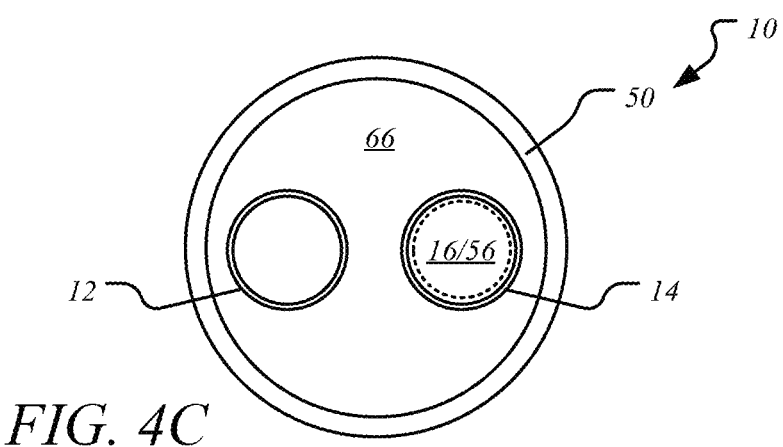
FIG. 4C is a top view of the rotatable ventilator adaptor in a second position.

In one embodiment, a ventilator adaptor 10 may have no intermediary position of the outlet between the first position 18 and the second position 20 that establishes fluid communication simultaneously among the first inlet 12, the second inlet 14, and the outlet 16. Again, this characteristic depends on the spacing of the inlets relative to the range of the outlet's movement. FIGS. 4A and 4C show first 52 and second 56 positions of the outlet, respectively. Here, no intermediary positions are able to establish fluid communication simultaneously among the inlets 12/14 and the outlet 16. An example intermediary position 54 which does not allow fluid communication between the outlet 16 and both inlets 12/14 is shown in FIG. 4B. Preferably, this intermediary position 54 exists only because of design choices in the ventilator adaptor 10, as the position is experienced only transiently while someone is quickly switching between first 52 and second 56 positions. Preferably, a patient having maintained lung recruitment using the ventilator adaptor 10 with ventilators may not experience this intermediary position for longer than 5 seconds. However, in an alternative embodiment, such an intermediary position may be used intentionally to prevent fluid communication to the outlet 16, essentially closing the ventilator adaptor 10.

In one embodiment, the ventilator adaptor 10 has a switch 30 to lock the first movable element 18 relative to the second movable element 20. The switch may be used to lock the outlet 16 in the first position 52 or the second position 56. Locking the outlet in either position may prevent accidental movement of the outlet when being used in a ventilator circuit. In one embodiment, the switch 30 may be a sliding panel having lengths and widths of about 0.5-2.5 cm, preferably 0.8-2.1 cm, more preferably 0.8-1.2 cm. The switch 30, as a sliding panel, may be held or secured in grooves within the first movable element 18 or the second movable element 20, and a portion may be moved into a complementary notch 32 or slot in order to prevent movement of the other movable element. FIG. 1 shows such a switch 30, which here is in an unlocked position. The exterior surface of the switch 30 may be patterned with grooves, ribs, knurls, or some other texture in order to facilitate a finger grip. Other types of switches 30 may be configured to lock the outlet 16 in the first position 52 or the second position 56. For example, a switch may comprise an axle with a cam housed in one movable element. Rotating the axle by an exterior knob may insert the cam into a slot in the opposing movable element, or the cam may slide a piston into the opposing movable element. In other embodiments, locking the outlet 16 in the first position 52 or the second position 56 may be possible by pressing the outlet 16 partially into the first movable element 18, or the first 18 or second 20 movable elements may have clamps, clips, or some similar structure to allow a user to temporarily limit movement.

In one embodiment, the ventilator adaptor 10 has a label, a notch, or a groove to indicate an alignment of the first movable element 18 relative to the second movable element 20. One or more of a label, notch, or groove may indicate an alignment that places the outlet 16 in the first position 52, the second position 56, or an intermediary position 54/76. For instance, one or both movable elements 18/20 may have lines, arrows, arrowheads, or shapes that can align and indicate the relative positions of the first movable element 18 to the second movable element 20 that place the outlet 16 in the first position 52 or second position 56. FIG. 1 shows a ventilator adaptor 10 with arrowheads 34. Labels on either movable element 18/20 may be textured, raised, depressed, or flush with the exterior surface of the movable element. In an alternative embodiment, a ventilator adaptor 10 may use electronic circuitry with one or more LED indicator lights to indicate the outlet 16 in the first position 52, a second position 56, or an intermediary position 54/76.

Depending on the structure of the switch 30, an additional label, notch, or groove may not be necessary. For instance, where the switch 30 is a sliding panel that slides into a notch 32, such as in FIG. 1, either movable element would have at least two notches, which may be sufficiently visible to indicate the outlet 16 being in the first 52 or second position 56.

In one embodiment, a ventilator adaptor 10 with rotatable first 18 and second 20 movable elements may not be shaped as a disc but instead as a different shape having two-fold rotational symmetry, such as a generalized cylinder having an elliptical base or a rectangular prism having a non-square base. In this embodiment, a label, notch, groove, or other marking may not be needed to designate when a 180° rotation is achieved, as it would be easily evident by the shape of the movable elements. Preferably, in this embodiment, the ventilator adaptor is able to maintain a closed ventilation system while the first 18 and second 20 movable elements are being rotated.

In one embodiment, the first movable element 18 is slidable relative to the second movable element 20 to align the outlet 16 with the first inlet 12 in the first position 52 or the second inlet 14 in the second position 56. These embodiments are illustrated in FIGS. 5A, 5B, 6, and 7A-7C. In FIGS. 5B and 7A-7C, the second movable element 20 is a flat panel to which the outlet 16 is connected. Two opposing edges of the panel are shaped to fit into the two grooves made by the linear inwardly-directed lip 58 of the first movable element 18. Here, the second movable element 20 may be moved by putting force on either side of the outlet 16, though in a related embodiment, the second movable element 20 may have a tab or some other structure for a user to handle directly. In another embodiment, the movable elements 18/20 may be spring-loaded, so that force is required to compress or stretch a spring in one direction, while the spring relieves force in the other direction. In one embodiment, as shown in FIGS. 7A-7B, bars 74 on the first movable element 18 may connect the bottom edges 58, while going underneath the second movable element 20. These bars 74 may be placed to be adjacent to one side of the outlet 16 in either first position 52 or second position 56. These bars 74 may allow proper alignment of the second movable element 20, as a user may slide the second movable element 20 until a bar 74 contacts the outlet 16, which would prevent further sliding movement. Alternatively, a raised structure attached to the underside of the second movable element may be used to contact the bar 74, rather than the outlet 16 itself. In alternative embodiments, the ventilator adaptor 10 may comprise or be attached to tracks, rails, gears, ball bearings, wheels, or other mechanical structures to assist in a controlled sliding movement.

In one embodiment, the first movable element 18 is rotatable relative to the second movable element 20 to align the outlet 16 with the first inlet 12 in the first position 52 or the second inlet 14 in the second position 56. The movable elements 18/20 may be rotated in a right or left-handed direction, though in one embodiment, the ventilator adaptor 10 may have a ratchet to only allow rotation in one direction. In another embodiment, either or both movable elements 18/20 may be structured with an additional groove or channel that limits the maximum rotation to a certain number of degrees, for instance, to a 178°-182° maximum rotation, or a 118°-122° maximum rotation.

In a further embodiment, where the first 18 and second 20 movable elements are rotatable relative to each other, the first movable element 18 and the second movable element 20 are disc-shaped, and either or both may have thicknesses of 0.6-2.6 cm, preferably 0.8-2.0 cm, more preferably 0.9-1.5 cm and diameters of 4.0-10 cm, preferably 4.5-8 cm, more preferably 4.8-6 cm. As mentioned previously, in one embodiment, where the first movable element 18 and the second movable element 20 are rotatable relative to each other, the first and/or second movable elements may have other shapes such as a generalized cylinder having an elliptical base or a rectangular prism having a non-square base, in order to identify rotation positions. In other embodiments, the first 18 and second 20 movable elements may meet with circular faces, but with opposing sides being curved, for example, where either or both elements may have spherical curves (such as a spherical cap or spherical segment). In other embodiments, either or both movable elements 18/20 may have angled edges, or a combination of angular, flat, and/or curved surfaces. In one embodiment, where the inlets 12/14 are angled away from each other, the outer surface of the inlets may be merged together and formed with the first movable element 18. In a further embodiment, where the outer surfaces of the inlets are merged together, the top 66 of the first movable element may have no surface substantially parallel to the inlet junction 64.

FIGS. 1, 2, 3A, 3B, and 4A-4C show ventilator adaptors 10 where the first 18 and second 20 movable elements are rotatable relative to each other. In these figures, the first 18 and second 20 movable elements are furthermore disc-shaped. Rotatable first 18 and second 20 movable elements may be attached by means of one movable element having an annular inwardly directed radial lip, which surrounds a circumference of the other movable element. For example, FIGS. 4A-4C show an annular inwardly directed radial lip 50 of the second movable element surrounding a circumference of the top of the first movable element 66. Alternatively, the lip may be a part of the first movable element, or may comprise a series of inwardly directed tabs, rather than a continuous lip. In another embodiment, an annular collar 48 may fit into annular grooves on both first 18 and second 20 movable elements, as shown in FIGS. 3A and 3B, which annular collar holds the movable elements together while allowing rotatable motion. In one embodiment, the movable elements may comprise a rounded bead and an annular groove that may be rotatable, and also removably attached, similar to a lid on a disposable coffee cup. In another embodiment, rotatable first 18 and second 20 movable elements may be attached through a central axle. Rotatable first 18 and second 20 movable elements may comprise or be attached to tracks, rails, gears, ball bearings, wheels, or other mechanical structures to assist in controlled movement.

According to a third aspect, the present disclosure relates to a method for switching between ventilator devices 78/80 with the ventilation assembly 100 of the second aspect, while maintaining respiratory support through the endotracheal tube 36. This method involves providing respiratory support by fluidly connecting the endotracheal tube 36 with a first ventilator device 78 fluidly connected to the first inlet 12, wherein the outlet 16 is in the first position 52; connecting a second ventilator device 80 to the second inlet 14; moving the outlet 16 from the first position 52 to the second position 56, thereby providing respiratory support by fluidly connecting the endotracheal tube 36 with the second ventilator device 80; and disconnecting the first ventilator device 78 from the first inlet 12.

In one embodiment of the method, the first ventilator device 78 is a mechanical ventilator 84, and the second ventilator device 80 is a manual resuscitator device 86. FIG. 8 shows this embodiment, where ventilator devices 78/80 have 22F connectors 82 to connect with the ventilator adaptor 10. Following the method as described earlier, the mechanical ventilator 84 is attached to the ventilation assembly 100 and provides respiratory support. The manual resuscitator device 86 is attached to the ventilator adaptor 10 by movement A. The outlet is switched between first and second positions by rotation as shown in B. The mechanical ventilator 84 may then be detached by movement C.

However, in a related embodiment, the first ventilator device 78 is a manual resuscitator device 86, and the second ventilator device 80 is a mechanical ventilator 84. In other related embodiments, different combinations and types of ventilator devices, such as those previously mentioned, may be attached to the ventilator adaptor 10 for the purpose of switching between ventilator devices. In another embodiment, first 78 and second 80 ventilator devices may be left attached to the inlets 12/14 with no disconnecting, and in a further embodiment of this, the outlet 16 may be moved back and forth between second 56 and first 52 positions as needed.

In one embodiment of the method, the endotracheal tube 36 is disposed within a patient 88, as shown in FIG. 8, and a lung recruitment of the patient 88 is maintained from before the moving to after the moving. Here, the ventilator adaptor 10 is able to switch between operating ventilator devices 78/80 without interruption to the patient 88, while providing respiratory support. Preferably this switching is done within a short time interval, for example, of less than 1.5 seconds, preferably less than 1 second, more preferably less than 0.8 seconds in order to maintain respiratory support through the outlet 16. However, in embodiments where intermediary positions 76 of the outlet 16 allow simultaneous fluid communication among inlets 12/14 and outlet 16, such as that discussed with FIG. 7B, it may be possible to switch between ventilator devices 78/80 more slowly than 1.5 seconds while providing respiratory support through the outlet 16. Preferably the switching is done by a medical professional, though a patient 88 using a ventilator at home may be able to use the ventilator adaptor 10 to switch ventilator devices by his or herself, or have a caregiver do so. Preferably, throughout the method of switching, the respiratory support is maintained as a closed system, which reduces the risk of ventilator associated pneumonia (VAP). By reducing the risk of VAP, the total intensive care unit and hospital stay cost may be reduced. In another alternative embodiment, the ventilator adaptor 10 may be housed in a machine or may have mechanical elements to move the outlet 16 from the first position 52 to the second position 56. In this embodiment, a person does not need to directly handle the ventilator adaptor 10.

As defined here, "providing respiratory support," means that an unimpeded flow of air is delivered to one or both lungs 90 of a patient 88. As mentioned previously, this includes air enriched in oxygen, or air mixed with water vapor or vaporous medicines. "Providing respiratory support" is analogous to maintaining or providing lung recruitment of a patient 88, meaning that the lung 90 does not collapse, and that respiratory failure is prevented.

In a preferred embodiment, the patient 88 is a human, but in other embodiments, the patient 88 may be a non-human mammal, including, but not limited to, dogs, cats, horses, and elephants.

The invention claimed is:

1. A ventilator system, comprising:
   a manual resuscitator device,
   a mechanical ventilator selected from the group consisting of a transport ventilator, an intensive-care ventilator and a neonatal ventilator, and
   a ventilator adaptor, comprising:
      a first movable element having a first inlet and a second inlet on an outer surface, wherein the first movable element has a concave inner surface opposite the outer surface; and
      a second movable element movably attached to the first movable element and having an outlet tube extending in an opposite direction from the first movable element, wherein the second movable element has an outer surface opposite the outlet tube matching the concave inner surface of the first movable element, wherein the inner surface of the first movable element includes circumferential grooves surrounding the first inlet and the second inlet, each groove configured to hold an o-ring in compression between the inner surface of the first movable element and the outer surface of the second movable element and separate the inner surface of the first movable element and the outer surface of the second movable element by a gap of 0.2-2 mm, wherein the first movable element has an integral annular inwardly directed radial lip that fits into an annular radial groove around the circumference of the second movable element, wherein the outlet tube has an inner diameter of 14.5-15.5 mm, wherein the first inlet and the second inlet have an outer diameter of 14.5-15.5 mm, and whereby the outlet tube is in fluid communication with the first inlet in a first position or is in fluid communication with the second inlet in a second position by moving the second movable element relative to the first movable element thereby aligning the outlet tube with the first inlet or the second inlet, and wherein the first movable element is rotatable relative to the second movable element to align the outlet tube with the first inlet in the first position or the second inlet in the second position, wherein the mechanical ventilator is attached to the first inlet and the manual resuscitator device is attached to the second inlet.

2. The ventilator system of claim 1, wherein a first central axis of the first inlet, a second central axis of the second inlet, or both forms an angle of 50°-80° with the surface.

3. The ventilator system of claim 1, which, other than the first inlet, the second inlet, and the outlet tube, does not have an additional inlet or outlet.

4. The ventilator system of claim 1, further comprising a label, a notch, or a groove to indicate an alignment of the first movable element with respect to the second movable element in the first position or in the second position.

5. A ventilation assembly, comprising:
the ventilator system of claim 1 and
an endotracheal tube removably attached to the outlet tube.

6. The ventilator adaptor of claim 1, wherein no collar is present around the circumference of the first or second movable element.

* * * * *